(12) United States Patent
Howard

(10) Patent No.: US 6,238,673 B1
(45) Date of Patent: May 29, 2001

(54) METHOD OF PRODUCING HIGH FLAVONOL CONTENT POLYPHENOL COMPOSITIONS

(75) Inventor: Alan Norman Howard, Cambridge (GB)

(73) Assignee: The Howard Foundation, Cambridge (GB)

( * ) Notice: Subject to any disclaimer, the term of this patent is extended or adjusted under 35 U.S.C. 154(b) by 0 days.

(21) Appl. No.: 09/311,300

(22) Filed: May 14, 1999

Related U.S. Application Data

(63) Continuation-in-part of application No. 08/934,128, filed on Sep. 19, 1997, now abandoned.

(30) Foreign Application Priority Data

| Sep. 20, 1996 | (GB) | 9619700 |
| May 31, 1997 | (GB) | 9711171 |
| May 31, 1997 | (GB) | 9711172 |
| May 31, 1997 | (GB) | 9711173 |

(51) Int. Cl.[7] ............... A61K 9/14; A61K 35/78
(52) U.S. Cl. .............. 424/195.1; 426/424; 426/490; 426/440
(58) Field of Search .............. 424/195.1; 426/424, 426/490

(56) References Cited

U.S. PATENT DOCUMENTS

| 3,294,637 | * | 12/1966 | Cervelle | 424/195.1 |
| 3,847,899 | * | 11/1974 | Mitchell | 424/195.1 |
| 4,004,038 | | 1/1977 | Wickrenmasinghe . | |
| 4,302,200 | | 11/1981 | Yokoyama et al. . | |
| 4,320,009 | | 3/1982 | Hilton et al. . | |
| 4,452,822 | | 6/1984 | Shrikhande . | |
| 4,481,226 | | 11/1984 | Crosby et al. . | |
| 4,500,556 | | 2/1985 | Langston . | |
| 4,698,360 | | 10/1987 | Masquelier . | |
| 4,820,420 | | 4/1989 | Hums . | |
| 4,857,327 | | 8/1989 | Virdalm . | |
| 4,913,909 | | 4/1990 | Hara . | |
| 4,975,297 | | 12/1990 | Gresch . | |
| 5,141,611 | | 8/1992 | Ford . | |
| 5,200,186 | | 4/1993 | Gabetta . | |

(List continued on next page.)

FOREIGN PATENT DOCUMENTS

| 0 169 347 | 1/1986 | (EP) . | |
| 0 216 936 | 4/1987 | (EP) | C07D/311/62 |
| 0 267 630 | 5/1988 | (EP) . | |
| 0 348 781 | 1/1990 | (EP) | A61K/35/78 |
| 0 384 796 | 8/1990 | (EP) . | |
| 0 692 480 A1 | 1/1996 | (EP) . | |
| 2161331 | * 7/1973 | (FR) . | |
| 1 092 269 | 11/1967 | (GB) . | |
| 1 195 050 | 6/1970 | (GB) . | |
| 1 349 483 | 4/1974 | (GB) . | |
| WO 94/22321 | 10/1994 | (WO) . | |
| WO 95/13360 | 5/1995 | (WO) . | |
| WO 96/13179 | 5/1996 | (WO) . | |

OTHER PUBLICATIONS

C.A. 109:168820 E. Revilla et al 1988.*
C.A. 69:26013 M. Bourzeit et al 1967.*
Frankel, E.N., et al., "Principle Phenolic Phytochemicals in Selected California Wines and Their Antioxidant Activity in Inhibiting Oxidation of Human Low–Density Lipoproteins", J. Agric. Food Chem., 1995, 43, 890–894.

(List continued on next page.)

Primary Examiner—Peter F. Kulkosky
(74) Attorney, Agent, or Firm—Pillsbury Winthrop LLP

(57) ABSTRACT

Disclosed is a method of producing a polyphenol-containing composition derived from grapes, the method including: preparing a liquid grape extract which includes polyphenols; contacting the liquid extract with a separation medium which fractionates the components of the extract; and recovering that fraction in which the polyphenols are present. Also disclosed is a method of enriching the composition with added flavonol.

20 Claims, 1 Drawing Sheet

U.S. PATENT DOCUMENTS

| | | |
|---|---|---|
| 5,352,384 | 10/1994 | Shen . |
| 5,464,619 | 11/1995 | Kuznicki . |
| 5,470,589 | 11/1995 | Shi . |
| 5,474,774 | 12/1995 | Walker . |
| 5,484,594 | 1/1996 | Frangi et al. . |
| 5,525,341 | 6/1996 | Walker . |
| 5,554,645 | 9/1996 | Romanczyk . |
| 5,587,176 | 12/1996 | Warren . |
| 5,591,771 | 1/1997 | Markonius . |
| 5,607,965 | 3/1997 | Kondo . |
| 5,637,561 | 6/1997 | Shen . |
| 5,650,000 | 7/1997 | Shuey . |
| 5,650,432 | 7/1997 | Walker . |
| 5,686,082 | 11/1997 | N'Guyen . |
| 5,700,468 | 12/1997 | Bombardelli . |
| 5,763,389 | 6/1998 | Shen . |
| 5,773,005 | 6/1998 | Takahashi . |
| 5,780,060 | 7/1998 | Levy . |

OTHER PUBLICATIONS

Hertog et al., "*Flavonoid Intake and Long–term Risk of Coronoary Heart Disease and Cancer in the Seven Countries Study*", Archives of Internal Medicine, 1995, 155, pp. 381–386.

Macheix et al., Fruit Phenolics, 1990, p. 3; p. 125.

Price et al., "*Cluster Sun Exposure and Quercetin in Pinot noir Grapes and Wine*", American Journal of Enology and Viticulture, 1995, 46, pp. 187–194.

Singleton et al., "*Colorimetry Of Total Phenolics with Phosphomolybdic–Phosphotungstic Acid Reagents*", American Journal of Enology and Viticulture, 1965, 16, pp. 144–158.

Salagoity–Auguste et al., Computer Abstract FSTA 85(05):H0058 "Wine Phenolics–analysis of low molecular weight components by high performance liquid chromatography" Journal Science of Food and Agric (1984) 35, (11) pp. 1241–1247.

Cheynier et al., Computer Abstract FSTA 87(6):H0073 "HPLC separation and characterization of flavonols in the skins of *vinifera* var. *Cinsault*" Amer. Journ. Enology and Viticulture (1986) 37 (4) pp. 248–252.

Oszmianski et al., Computer Abstract BIOSIS 88:438868 "Fractionation of Phenolic Compounds in Red Wine", American Journ. Enology and Viticulture, (1988) 39 (3), pp. 259–262.

Tomasbarberan et al., Computer Abstract SCISEARCH 92:543473, "Phytochemical Analysis", (Jul./Aug. 1992) vol. 3, No. 4, pp. 178–181.

Database WPI, Derwent Publications Ltd, Section Ch, Week 9537, JP 07 179 489 A, Jul. 18, 1995.

\* cited by examiner

US 6,238,673 B1

METHOD OF PRODUCING HIGH FLAVONOL CONTENT POLYPHENOL COMPOSITIONS

This is a Continuation-in-Part of National application Ser. No. 08/934,128 filed Sep. 19, 1997, now abandoned.

FIELD OF THE INVENTION

This invention relates to a method of producing polyphenol-containing compositions.

BACKGROUND TO THE INVENTION

Polyphenols are those compounds which comprise more than one phenolic group. Among the polyphenols are the following classes: flavonoids (a term often used to denote polyphenols in general, but more commonly in Europe to denote only the flavones), the flavanols, proanthocyanidins (also called procyanidols, procyanins, procyanidins and tannins) and anthocyanins.

The flavones are compounds with a basis structure shown in FIG. 1 in which two benzene rings (A and B) are linked with a heterocyclic six member ring C containing a carbonyl ring. Ring B can be joined in position 2 (as illustrated) to give a flavone or to position 3 to give an iso flavone. Hydroxylation can occur at positions 3, 5, 7, and 3', 4', 5' to give compounds called flavonols. Typical examples of flavonols are: quercetin (hydroxylated at positions 3, 5, 7, 3', 4'), kaempferol (hydroxylated at positions 3, 5, 7, 4') and myricetin (hydroxylated at positions 3, 5, 7, 3', 4', 5'). They can exist naturally as the aglycone or as O-glycosides (e.g. D-glucose, galactose, arabinose, rhamnose, etc). Other forms of substitution such as methylation, sulphation and malonylation are also found.

The flavanols have a basic structure shown in FIG. 2. The two most common flavanols are catechin (hydroxyl groups positions 5, 7, 3', 4') and its stereo-isomer epicatechin. The hydroxyl groups can be esterified with gallic acid. The proanthocyanidins are polymers of catechin and/or epicatechin and can contain up to 8 units or more. These compounds are often called proanthocyanidins, procyanidins or tannins.

The anthocyanins are colored substances, sometimes called anthocyanidins. Typical examples are: cyanidin (hydroxylated at positions 3, 5, 7, 3', 4'), delphinidin (hydroxylated at positions 3, 5, 7, 4', 5') and pelargonidin (hydroxylated at positions 3, 5, 7, 3'). The hydroxyl groups are usually glycosylated and/or methoxylated (e.g. malvidin at 3', 5').

Within the general term "polyphenols" are included the dihydroxy-or-tri-hydroxy benzoic acids and the phytoalexins, a typical example of which is resveratrol.

Polyphenols are found in various amounts in large numbers of natural products especially plant material such as fruit and vegetables. A particular rich source are grapes, in which the polyphenols are plentiful in the skins and seeds, but not in the pulp. During the manufacture of grape juice, quantities of polyphenols are expressed into the juice, and the polyphenol content will depend on the type of grape, the climate in which it is grown, and the manufacturing process used in making the juice. Some grape juice, especially that made from the Concord grape, may contain as much as 2.5 g/L polyphenol. Grape skins and seeds are commercially extracted with water and other solvents to obtain polyphenols. In particular polyphenols from grape skins and seeds become incorporated into wine during the vinification process. Red wine is made by maintaining contact between the fermenting liquor and the crushed grape residue (pomace) for prolonged periods, while in the manufacture of white wine the grape skins are removed relatively quickly. Accordingly, wine in general, and red wine in particular, contains reasonable amounts of polyphenols, amounting to about 1–3 g/L and is thus a potential commercial source of polyphenolic compounds.

Polyphenols are known to have antioxidant properties and have potential use in the food, cosmetic and pharmaceutical industries. However, in order for polyphenols to be used commercially the polyphenols have to be separated from grape extracts and wine in a more concentrated form. Dealcoholised wine has been available for many years and can be concentrated by distillation. Also it is possible under certain conditions to obtain a dry power from dealcoholised wine by spray drying.

Among the polyphenols, the flavonols have been shown to have many useful properties as antioxidants, and to decrease platelet stickiness. Epidemiological studies have shown that countries and people with a high flavonol intake have less coronary heart disease (Hertog M G L et al., 1995, Arch Int Med 155, 381–6).

Flavonols are present in grapes and values ranging from 8 to 97 mg/Kg FW have been reported (Macheix et al., 1990 Fruit Phenolics pp. 378 CRC Press Boca Raton). In grape skins the flavonols occur as the glycosides and the free aglycone is not present. During the fermentation process, some of the sugar is split off and the aglycone formed. On average about 50% of the flavonol exists in wine as the aglycone. It has been discovered that the flavonol content of grape skins and wine is very variable and depends on the variety of grape and more especially the amount of sunshine in which the grapes are grown. The flavonols have a yellow color and act as filters to blue and ultraviolet light which is very injurious to the grape. During period of intense sunlight more flavonols are synthesized to protect the grape, and consequently the grape skins and the wine from which it is made has a high concentration of flavonols. (Price S F et al., Am J. Enol Vitic 46 187–194, 1995).

Some wines in France have only 5 mg/L flavonol (calculated as aglycone) whereas up to 150 mg/L have been reported in some Californian wines. The flavonols are virtually absent from the pulp and grape seeds and only trace quantities are present in commercial anthocyanin powders extracted from pomace after making red wine.

Wine contains many substances besides alcohol and polyphenols; these may include carbohydrates, especially glucose, tartaric acid and mineral salts. A typical red wine contains about 23 g/L solids and 1.5 g/L polyphenols. For commercial use it would be preferable that the polyphenols should be in a stable and easily transportable form and more preferably as a solid. In solution, especially in dealcoholised wine, the polyphenols are capable of being oxidized, and contaminated with micro-organisms. A method is therefore needed to isolate the total polyphenols in wine from the other constituents.

Although grape juice is often less rich in polyphenols than wine, it is a readily available commodity, and can be used as a source of polyphenols. It has a high sugar content and a high content of solids.

It would also be a great advantage to use, as a source of polyphenols, by-products of the wine-making process such as grape skins or wine pomace (a mixture of skins and seeds obtained after pressing the grapes to obtain the juice). Pomace contains grape seeds which have been used extensively in the industry to obtain grape seed oil, and polyphenols. Two such products containing polyphenols are Endotenol™ (Sanofi-Labaz, France) and Activin™ (Interhealth Nutritionals Inc., California, USA).

Grape seeds contain chiefly one class of polyphenols, the proanthocyanidins, with catechin, epcatechin and their esters as minor components. The material obtained from grape seed does not have such a wide spectrum of polyphenols as are present in wine or grape skins. Grape seed extract is unsuitable for preparing a "total phenolic pool" and does not protect low density lipoproteins from oxidation in vivo.

Grape skins before fermentation contain more of the flavonols present in the whole grape. When red wine is made flavonols are leached out of the skins and seeds by the aqueous ethanol and the pomace will be depleted of some of the flavonols. In white wine manufacture, the skins and seeds are not usually present during the fermentation process and most of the flavonols are left in the pomace.

Those skilled in the art can predict that to develop a manufacturing procedure will not be straightforward. Presented with a complex mixture of organic and inorganic chemical as in grape juice, wine, grape skins and pomace the possibility of obtaining a high concentration of polyphenols and flavonols initially present as only about 5–10% and 0.1–0.2% of the total solids respectively represents a challenge which would need inventive skills. Further, the desirability of developing such a process would not be obvious.

Polyphenols are a mixture of substances of very different molecular weight and polarity. They are known to be soluble or partly soluble in polar solvents or admixtures thereof (e.g., water, ethanol, methanol, acetone, ethyl acetate). Also certain resins such as Sephadex LH-20 have been used for the purpose of separating polyphenols for analysis by thin layer, column and HPL chromatography.

Various methods have been developed to extract polyphenols from grape skins, especially from red or black grapes since the anthocyanin pigment is used as a colorant in foods. The methods so far disclosed have not been directed to obtaining a polyphenol extract with a high flavonol content. Flavonols are not present in grape seeds, and these have been extracted chiefly to obtain the proanthocyanidins.

Yokoyama et al. (U.S. Pat. No. 4,302,200) discloses a process for extracting anthocyanin-type color from natural products (grapes) which includes contacting the natural product with a sulfite ion-containing aqueous solution at a temperature of about 85° C. or higher. Yokoyama et al. discloses a process suited to the recovery of anthocyanin, but not flavonols.

Hilton et al. (U.S. Pat. No. 4,320,009) discloses a process for obtaining anthocyanin pigment extracts in which large quantities of anthocyanin extract may be obtained from grape skin residue from wine fermentation. The latter would not contain the flavonols which are eluted from grape skins during the wine making process. In the method of Hilton et al. it is necessary to add filler such as maltodextrin before spray drying grape skin extracts. Such a method would give low concentration of polyphenols in the final composition.

Although Hilton et al. discloses a process for obtaining anthocyanins which includes preparing an aqueous grape skin extract, absorption of the pigments onto an ion exchange resin, elution from the resin, and if necessary, further chromatography on paper or a thin layer of silica gel, the process is entirely focused on obtaining anthocyanin and, as a result, flavonols would not be recovered.

Shrikhande (U.S. Pat. No. 4,452,822) discloses a process for improvements in the production of anthocyanin coloring material from red grape pomace or other anthocyanin sources using extraction with sulfur dioxide. The improvement is to treat the sulfur dioxide extract enzymatically to reduce or eliminate the solid material present in the extract. The method involves the use of $H_2O_2$ which would oxidize and destroy flavonols.

Crosby et al. (U.S. Pat. No. 4,481,226) discloses a stabilized anthocyanin grape extract colorant. The stabilized product is made by combining tannic acid and anthocyanin grape extract colorant in an appropriate solvent, and recovering the product. The method is not directed to the recovery of flavonols.

Langston (U.S. Pat. No. 4,500,556) discloses a process for obtaining anthocyanin colorant by extraction from grape pomace. The method described in Langston is to contact grape pomace with $HSO_3$ to form a complex. The complex is recovered by treating the liquid extract phase with a non-ionic adsorbent to adsorb the complex. The adsorbent bed is rinsed with water to remove the adsorbent water-soluble non-pigment material, such as sugar, organic acid and solid particles. The complex is then eluted from the adsorbent with an acidified organic solvent leaving the polymerized anthocyanin pigment behind. The preferred solvent is 100% ethanol acidified with a small amount of mineral acid which breaks the complex such that the anthocyanin free of $HSO_3$ ions is eluted. The process is not directed to the recovery of flavonols, which would be destroyed therein.

Ford (U.S. Pat. No. 5,141,611) discloses a process for removing polyphenolic substances from a solution by adsorption on a polyamide resin having a specific porosity and extended surface. The process is not directed to the recovery of flavonols.

Frangi et al. (U.S. Pat. No. 5,484,594) discloses procyanidol oligomeric fractions extracted from vegetables and uses grape seeds as the starting material. The process does not include the isolation of flavonols which would be destroyed during the process if present.

Salagoity-Auguste et al. (J. Sci. Food and Agric. 1984 35 1241–1247) discloses an analytical process by which de-alcoholised wine was extracted with ethyl acetate which did not extract the anthocyanidins and gave a low yield of procyanidins. The extracts were removed from a column (C18 hydrocarbon polymer) with a solution containing perchloric acid. The method is not suitable for the preparation and isolation of polyphenols from grape extracts for human consumption.

Cheynier et al. (Am. J. Enol. Vitic. 1986 37 248–252) discloses a method whereby the skins were extracted with methanol and the solvent removed. The method used ethyl acetate to remove anthocyanins and the extract was then fractionated on a polyamide column.

Acetonitrile used in the chromatographic separation is an unsuitable solvent for food extraction methods and is not "Generally Recognized as Safe" (GRAS). Its use in food is not permitted.

Oszianski et al. (Am. J. Enol. Vitic. 1988 39 259–262) discloses a method of fractionation with is a Sep-Pak cartridge and also uses acetonitrile as a solvent.

Tomas-Barberan et al. (Phytochem. Anal. 1992, 3 178–181) uses synthetic mixtures of flavonols in an aqueous solution not grape extracts. Other polyphenols in grape extract were not studied or disclosed.

To summarize, many methods of extracting polyphenols have been developed but all of these have been directed towards obtaining anthocyanins, procyanidins or polyphenols other than flavonols, and/or are not suitable for preparing compositions for human consumption.

What is needed, therefore, is a method of extracting polyphenols which contain substantial amounts of flavonols and preparing compositions therefrom which are suitable for human consumption.

SUMMARY OF THE INVENTION

The inventor has found rather surprisingly that it is possible to select grape juice, wine, dealcoholised wine or grape skin extract containing substantial amounts of flavonols and to manufacture from these the polyphenols to give a product with a high concentration of polyphenols (typically about 45% w/w), of which flavonols comprises at least 2% w/w of the polyphenols present. Such a composition is found to be suitable for human consumption.

It has also been found possible to take grape juice, wine, dealcoholised wine, or grape skin extract and to manufacture therefrom polyphenols to which pure or relatively pure flavonols can be added to give a product with a high concentration of polyphenols (typically about 45% w/w), of which flavonols comprise at least 2% w/w of the total polyphenols present. Such a composition is found to be suitable for human consumption.

The present invention provides a method of producing dry polyphenol containing composition for human consumption comprising: contacting liquid grape extract with a non-oxidizing chromatographic separation medium which fractionates the components of the extract; eluting material from the separation medium with an eluent; recovering that fraction in which the polyphenols are present, wherein the recovered polyphenol fraction comprises at least 25% w/w polyphenols and the flavonol content is at least 2% w/w of the polyphenols; and drying the recovered polyphenol fraction.

DETAILED DESCRIPTION OF THE PRESENT INVENTION

Figure 1:
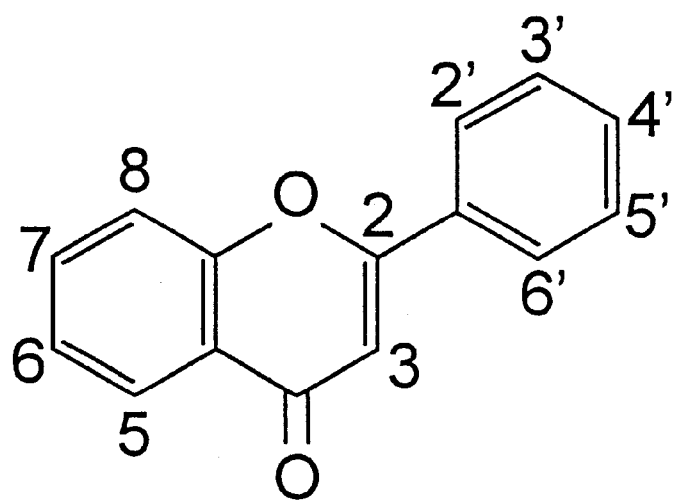
FIG. 1 shows the basic structure of the flavone.

The invention provides a method of manufacturing a dry polyphenol containing composition for human consumption, the method including contacting liquid grape extract with a non-oxidizing chromatographic separation medium which fractionates the components of the extract; eluting material from the separation medium with an eluent; recovering that fraction in which the polyphenols are present, wherein the recovered polyphenol fraction comprises at least 25% w/w polyphenols and the flavonol content is at least 2% w/w of the polyphenols; and drying the recovered polyphenol fraction.

The adsorption mechanism typically relies upon non-specific dipole-dipole interactions between the separation medium and the components of the liquid extract. The eluent (solvent) carries those molecules faster which are less tightly bound to the medium.

In preferred embodiments the separation medium is a chromatographic medium acceptable for use in the food industry. The medium is conveniently supported in a large (preparative)—scale chromatographic column. It may be possible to use natural polymeric media, such as microparticulate cellulose which is particularly well suited for the separation of nucleotides, sugars, amino acids and polyphenols. Potential drawbacks to the use of microparticulate cellulose or derivatives thereof, are swelling in an aqueous environment and/or compressibility under pressure. Other alternatives are silica gels, dextran polymers (e.g. Sephadex™ LH 20, Pharmacia UK) or agarose beads (e.g., Sepharose™, Pharmacia, UK).

Other alternative natural adsorbents include alumina, silica and hydroxyapatite; however these materials may be unacceptable for use in the food industry owing to the present of 'fines' (particles with diameters <20 $\mu$m).

More conveniently, the separation medium will comprise a synthetic polymeric resin. Generally these synthetic polymeric adsorbents take the form of non-ionic macroreticular resins that adsorb and releaser ionic and polar molecules (compounds) through hydrophobic and polar interactions; these are usually employed under isocratic conditions (i.e., only a single eluent of fixed composition is used).

Such polymeric resins are usually derived from a synthetic hydrophobic polyaromatic resin such as polyvinylbenzene (polystyrene). These resins are manufactured under trade names such as Diaion™, Amberlite™ and Dowex™. Indeed, a particularly preferred separation medium comprises Diaion HP20, a polystyrene resin. Even more preferred is Sepabeads™ SP70 since it is accepted for manufacturing food ingredients.

The advantage of using these resins is, that they have comparatively large surface areas (typically 450–900 $m^2g$) and high porosity (pore volume, typically 0.6–1.8 ml/G) and large average pore sizes (typically 100–800 A), which combined with a coarse particle size (typically 20–60 mesh, wet) allows for both high extract flow rates and large capacity for the retention of the compounds of interest.

Another advantage of the polystyrene resins is that the flavonols are especially well adsorbed when dissolved in water or dilute aqueous ethanol (e.g. 25% v/v ethanol).

Alternatively, it is possible that the moderately polar polyacrylate based resins could be employed. However, the selectivity for different polyphenols is unlikely to be the same.

Eluting solvents for elution from the polymeric resin may be any which are accepted for the preparation of food (e.g., water, methanol, ethanol, acetone, ethyl acetate, methylene dichloride, chloroform or mixtures thereof). The preferred solvent for elution is aqueous ethanol. A concentration of 75% ethanol v/v is preferred since it gives a very high yield of flavonols. Less preferred is 50% ethanol v/v which gives a lower yield.

The liquid grape extract may be unfermented (e.g., grape juice, grape skins) or fermented (e.g., wine, dealcoholised wine, grape skins, pomace). Particularly preferred is grape juice, dealcoholised red wine or an aqueous extract prepared from white wine pomace or grape skins.

It is preferred to use a liquid grape extract which is prepared substantially from grape skins, and not from grape seeds (unlike say, the process disclosed in U.S. Pat. No. 5,484,594).

It is preferred to choose a liquid grape extract containing substantial quantities of flavonols. The method of manufacture retains almost all the flavonols on the resin column which on elution gives a high yield of flavonols. The higher the flavonol content of the liquid grape extract the higher will be the flavonol content of the resulting polyphenol composition. A preferred grape extract is one that contains at least 10 mg flavonol/g polyphenol.

To choose a liquid grape extract that contain substantial quantities of flavonols it is desirable to measure the polyphenols therein. For this purpose a convenient method is to use HPLC analysis. After centrifugation of the liquid extract at 10,000×g for 3 min an aliquot is injected into an HPLC column and the major constituents estimated, for example by the method of Price et al. (Am. J. Enol. Vitic. 46 187–94, 1995), the full disclosure of which is herein incorporated by reference.

Total polyphenols are estimated according to the method of Singleton S L & Rossi J A (Am. J. Enol. Vitic, 16 144–158, 1965), the full disclosure of which is herein incorporated by reference.

The total flavonols are calculated as the aglycone. For instance, the flavonol quercetin (MW 302) and quercitrin (MW 448) a flavonol glycoside are conventionally used as HPLC standards. In this case the flavonol glycoside is 67% aglycone.

The composition is provided in dry form, preferably as a dry powder. Accordingly, the method of the invention incorporates a drying step. Various drying techniques are well known to those skilled in the art: for example, freeze drying; particularly preferred is spray drying.

Performance of the method of the present invention typically results in a composition comprising at least 25% w/w/ polyphenols, preferably at least 35%, more preferably at least 45%, and most preferably at least 50%. The polyphenol content will also contain flavonols. The flavonol content of the dry composition produced by the method of the invention will preferably be at least 1% w/w, more preferably at least 2%. In relation to the total polyphenol content of the composition, flavonols will preferably comprise at least 2% w/w polyphenols and more preferably at least 4% w/w polyphenols.

For practical and economic reasons a level of 2% w/w flavonol w/w polyphenols is preferred. This represents an intake of about 10 mg/day flavonol when 1 g/day of such a composition is consumed.

Compositions containing less than 2% w/w flavonol w/w total polyphenols will require very large doses to attain a therapeutic effect, provided by flavonols. If given in the form of capsules or tablets, the number to be taken will be larger than most people wish to consume. Of taken as a drink, the other polyphenols present in the composition especially the tannins would make the product unpalatable.

It is a particular object of this invention to manufacture a dry powder, containing polyphenols obtained from grape juice, wine, grape skin or pomace which is not highly contaminated with other constituents of the starting material. The polyphenol powder will desirably contain not more than 75% w/w contaminating substances present in the starting material. Typically red wine solids contain from 4% w/w to 12% w/w polyphenols.

A concentration of up to 25% w/w polyphenol in the resulting composition represents up to a two fold concentration of that present in the original wine or grape skin. Preferably the polyphenol powder will contain not more than 5% w/w to 65% w/w contaminating substances present in the starting material.

It is understood that in manufacturing practice it is possible to add fillers such as malto dextrin before spray drying. This gives a dry powder in which the polyphenols are diluted and which may be convenient for the preparation of soft drinks, and as an additive to food items. The starting material whether grape juice, wine, grape skins or pomace often has a low palatability because of the presence of mineral salts, tartaric acid and wine flavors. It is highly desirable to remove these from the polyphenols before their use in foods.

Grape juice and wine are high in calories and it would be an advantage to remove the sugar or alcohol to provide a product much lower in calories.

In a typical method of manufacture red wine is passed through an absorbent resin column. It is then eluted by aqueous alcohol, the alcohol removed, the mixture concentrated by heating and the residue spray dried. The resin employed can be any from which the polyphenols can be obtained by eluting with a solvent. Both resin and solvent should preferably be those which conform with good food manufacturing process and are permitted by Health Authorities. Typical resins which can be used include those listed above.

Wine, pure grape juice or grape juice diluted with water is also conveniently used. It is a great advantage to use wine or a juice which has a high polyphenol content. For dealcoholised wine, the alcohol is conveniently removed by distillation in vacuo. For grape skins or pomace, the material is mixed well with a suitable solvent preferably water or aqueous alcohol which can be heated to accelerate the extraction process. A clear solution is then obtained by either static decantation, centrifugation, or filtration (with or without the addition of a flocculent). The liquid can then be applied to a resin column in the same manner as described above for dealcoholised wine. The most preferred source is skin from grapes or pomace which has been used to make white wine since this material retains a high polyphenol content.

One aspect of the invention is to select a grape extract which will contain sufficient flavonols to yield at least 2% w/w of total flavonols (expressed as the aglycone) or 1% w/w flavonol dry composition.

Another aspect of the invention is to enrich the flavonol content of the composition by adding pure or relatively pure flavonols, as the aglycone or conjugated flavonol, during the process of manufacture.

It is preferable to use grape juice extracts which contain abundant flavonols. Because of the type of grape, climatic conditions in which it is grown, and the method of processing the grape material to obtain the extract, many grape extracts contain a low concentration of flavonols. In such cases it is preferred to enrich the composition with flavonols either as the pure substance or relatively pure substance.

Examples of flavonols which can be used are quercitin, myricetin and kaempferol either as the aglycone or the glycoside. Most preferred are quercitin dihydrate, quercitrin (the glycoside of quercitin) and rutin dihydrate (quercitin - 3 rutinoside). These are available pure from chemical suppliers. However the invention is not limited to pure compound and any suitable enriched material can be utilized.

In a typical method, a grape extract which is poor in flavonols is used and the polyphenols are separated by adsorption on a resin, and subsequently eluted. Enrichment of the final products is attained by adding the flavonol to any stage of the process, namely to the grape extract, to the absorbent resin, to the eluate, to the concentrated eluate or to the dry composition.

The preferred method is to dissolve the flavonol material in aqueous ethanol, for the purpose of enrichment, and then add the liquid at the chosen stage of manufacture.

A less preferred method is to dissolve the flavonol in one of the liquids used in the separation method by heating and mixing.

For mixing with the dry polyphenol composition, the ground solid materials can be mixed well in a rotary mixer so as to give a good distribution of flavonols in the total composition.

The amount of flavonol added is at least enough to give a concentration in the final composition of 2% flavonol w/w polyphenols.

The method of enrichment is not restricted to compositions containing sufficient flavonols to give a final composition of 2% flavonol w/w polyphenols. It can also be used to enrich any composition prepared as herein stated. It is preferred that the amount of flavonol added (expressed as aglycone) should be from 0.1% to 80% w/w polyphenols in the final composition. It is most preferred to add 1% to 25% w/w polyphenols to the final composition.

The purpose of enrichment is to provide an even higher intake of flavonol when the composition is used as a food supplement, than could be obtained using the composition obtained from grape extracts alone. It is a great advantage to have flavonols mixed with other polyphenols in grape extracts, since they act synergistically. For example, flavonols are not very soluble in water, but dissolve quite readily when mixed with other grape polyphenols especially those containing a high content of anthocyanins. This process renders the flavonols more bio-available.

Figure 2:
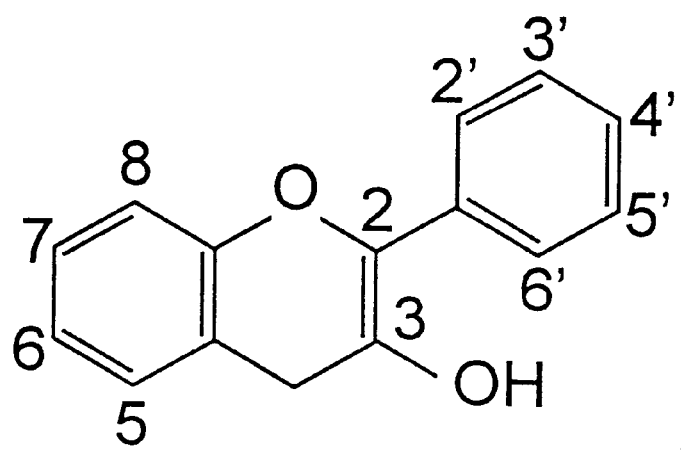
FIG. 2 shows the basic structure of a flavanol.

The invention will now be further described by way of illustrative examples and with reference to the accompanying drawings, in which:

FIGS. 1 and 2 show the basic chemical structures of certain polyphenol compounds.

EXAMPLE 1
Preparation of Composition from Red Wine with a High Flavonol Content

Californian Barbera red wine was chosen for the method of manufacture because of its flavonol high content. It contained 7.5 mg/L myricetin glycosides, 40.7 mg/L quercitin glycosides, 1.5 mg/L myricetin, 9.7 mg/L quercitin, 0.8 mg/L kaempferol. The total flavonol content was calculated as 44.3 mg aglycone/L. The wine had a total polyphenol content of 1.28 g/L.

The method of manufacture was as follows:

A 500 ml column of Diaion™ HP-20 resin was conditioned with 2 bed volumes (bv) of 12% alcohol (4.5 bv/hr). 5 L of Barbera wine were added slowly to the column (about 4–5 bv/hr) followed by a de-ionized water rinse (2 bv). The polyphenols were eluted with 1.1 L aqueous ethanol (75% v/v ethanol) and evaporated using a rotary evaporator under vacuum. A dry power was obtained by adding excess absolute ethanol and evaporating under vacuum. The process gave a red powder, readily soluble in water.

The polyphenol content of the red powder obtained was 60% w/w with a yield of 1.34 g powder/L wine.

The samples were analyzed by ETS Laboratories of St. Helena Calif. 94574 and the results are given in Table 1. The total flavonol content of the powder was 31.3 mg aglycone/g (3.13% w/w) or 5.2% flavonol w/w total polyphenols.

EXAMPLE 2
Preparation of Compositions Using Dealcoholised Wine

The same Barbera wine used in Example 1 was dealcoholised using a vacuum evaporator at 39° and 28 in vacuum. The initial volume was restored by the addition of deionized water. A column containing 500 g Diaion™ HP-20 resin was washed with deionized water (2 bv) and 5.4 L was passed down the column (4.5 bv/hr) and then

TABLE 1

Polyphenol concentrations in wine, dealcoholised wine, and the resulting powders obtained after absorption and elution from Diaion HP2O resin

| Polyphenol* | Barbera Wine Natural mg/L | Barbera Wine Dealcoholised- mg/L | Barbera Wine Natural Powder Obtained mg/g | Barbera Wine Dealcoholised Powder obtained mg/g |
|---|---|---|---|---|
| 1 gallic acid | 28.8 | 28.7 | 0.8 | 0.6 |
| 2 procyanidin dimers | 56.2 | 55.8 | 21.9 | 23.3 |
| 3 catechin | 35.2 | 31.8 | 10.2 | 13.9 |
| 4 epicatechin | 33.0 | 27.6 | 15.5 | 11.3 |
| 5 syringic acid | 4.9 | 5.6 | 4.2 | 2.2 |
| 6 polymeric phenols | 185 | 221 | 130 | 99.9 |
| 7 caftaric acid | 22.0 | 21.7 | 0.7 | 2.0 |
| 8 caffeic acid | 15.4 | 15.0 | 7.8 | 5.2 |
| 9 coutaric acid | 2.4 | 2.7 | <0.1 | 0.5 |
| 10 p-coumaric acid | 13.3 | 13.1 | 8.8 | 5.6 |
| 11 trans resveratrol | 13.1 | 12.5 | 9.1 | 5.6 |
| 12 cis resveratrol | 1.0 | 1.0 | 0.8 | 0.4 |
| 13 myricetin glycosides | 7.5 | 7.8 | 5.1 | 3.4 |
| 14 quercetin glycosides | 40.7 | 38.9 | 30.9 | 17.2 |
| 15 myricetin | 1.5 | 1.3 | 1.0 | 0.7 |
| 16 quercetin | 9.7 | 9.1 | 6.0 | 4.3 |
| 17 kaempferol | 0.8 | 0.7 | 0.3 | 0.3 |
| 18 delphinidin glycoside | <0.1 | <0.1 | <0.1 | <0.1 |
| 19 cyanidia glycoside | <0.1 | <0.1 | <0.1 | <0.1 |
| 20 peonidin glycoside | <0.1 | <0.1 | <0.1 | <0.1 |
| 21 petunidin glycoside | <0.1 | <0.1 | <0.1 | <0.1 |
| 22 malvidin glycoside | <0.1 | <0.1 | <0.1 | <0.1 |
| 23 delphinidin glycoside | 4.3 | 4.2 | <0.1 | 1.0 |
| 24 cyanidin glucoside | 2.1 | 1.6 | <0.1 | 0.8 |
| 25 peonidin glucoside | 8.4 | 8.4 | 0.8 | 3.5 |
| 26 peruridin glucoside | 4.7 | 4.4 | 0.8 | 1.9 |
| 27 malvidin glucoside | 74.9 | 73.3 | 12.7 | 31.5 |

TABLE 1-continued

Polyphenol concentrations in wine, dealcoholised wine, and the resulting powders obtained after absorption and elution from Diaion HP2O resin

| Polyphenol* | Barbera Wine Natural mg/L | Barbera Wine Dealcoholised+ mg/L | Barbera Wine Natural Powder Obtained mg/g | Barbera Wine Dealcoholised Powder obtained mg/g |
|---|---|---|---|---|
| 28 polymeric anthocyanins | 12.5 | 12.0 | 7.6 | 5.6 |

+Dealcoholised wine, made up to original volume with water
*Peaks 1 and 5 were quantified as gallic acid, peaks 2, 3, 4 and 6 as catechin, peaks 7 through 10 as caffeic acid, peaks 11 and 12 as trans resveratrol, peaks 13 and 14 as quercetrin, peaks 15, 16 and 17 as quercetin, and peaks 17 through 28 as malvin

TABLE 2

Yield of flavonols with different concentrations of aqueous ethanol as eluant

| | Example 2: 75% Ethanol | | Example 3: 50% Ethanol | |
|---|---|---|---|---|
| Flavonol | Yield mg/g Theoretical | Actual | Yield mg/g Theoretical | Actual |
| Myrecitin glycoside | 3.6 | 3.4 | 0.9 | <0.1 |
| Quercitin glycoside | 17.2 | 17.2 | 3.8 | 3.0 |
| Myrecitin | 0.6 | 0.7 | 0.5 | <0.1 |
| Quercitin | 4.1 | 4.2 | 0.5 | 0.1 | washed with deionized water (2 bv). Polyphenols were eluted with 1.3 L 75% aqueous ethanol (4.5 bv/hr) and the solution evaporated to dryness by a rotary evaporator, under vacuum as in Example 1. The yield of red power was 2.24 g/L wine, and it contained 57% w/w polyphenol. The flavonol content was 3.35% flavonol w/w polyphenols.

Assuming that there was no loss of flavonols an approximate estimate of the theoretical yield of flavonols can be obtained by dividing g/L in the dealcoholised wine by 2.2. A comparison of the theoretical with the actual analysis is shown in Table 2.

The yield of flavonols was excellent and the result indicates that the flavonols are well retained on the Diaion™ HP-20 resin column and that elution with 75% aqueous ethanol gives a high yield.

EXAMPLE 3
Preparation of Composition from a Red Wine Containing a Low Concentration of Flavonols and Enrichment with Pure Flavonol The red wine processed was of a Cabernet Sauvignon variety from France. It contained 1.8 g/L polyphenols. The flavonol content (calculated as the aglycone) was 8.8 mg/L (myricetin glycosides 1 mg/L, quercitin glycosides 5.4 mg/L, myricetin 1 mg/L. quercitin 1 mg/L).

The power containing the polyphenols was made as follows:

1 liter of red wine was filtered, rotary evaporated under reduced pressure at 75° C. for one minute, cooled, then rotary evaporated under reduced pressure at 55° C. until the volume was reduced to approximately 150 ml.

50 g of Diaion™ resin was weighted into a beaker, covered with methanol and allowed to stand for 15 minutes. The methanol was then decanted off, and replaced with water. After standing for 10 minutes the resin was packed into a glass column, half filling the column, and washed with water.

The wine concentration was applied to the column, followed by a water wash (300 ml). The polyphenols were eluted with 50% ethanol. Collection was begun as the colored fraction began to exit the column, and was ended when the eluate was free from color (after a total of 500 ml 50% ethanol had been used). Phenolic content of the eluate at this point was at a concentration of 0.1 mg/L as determined by the Folin-Ciocalteu method.

The phenolic fraction was reduced by rotary evaporation at 50° C. to approximately 120 ml and this was freeze-dried to give the final sample.

The yield of powder was 2.24 g/L with a polyphenol content of 45%. The flavonol content was only 4.5 mg aglycone/g polyphenols (0.45% w/w).

Assuming that there was no loss of flavonols, an approximate estimate of the theoretical yield of flavonols can be obtained by dividing g flavonol/L by 2.5. A comparison is shown in Table 2. The yield of flavonols obtained was only 50% when 50% v/v aqueous ethanol was used as the eluent.

This low yield has been confirmed with other dealcoholised wines containing over 10 mg aglycone/L (data not shown here).

Fortification of polyphenol powder with pure flavonol was made as follows: 400 g of the polyphenol powder was dissolved in 10 L deionized water. Quercitin dihydrate (Sigma Laboratories, UK) amounting to 12 g was dissolved in 3.5 L ethanol and added to the above to give a clear solution. The alcohol was removed by a rotary evaporator under vacuum, and the residue freeze-dried to give a solid with 3–4% moisture content.

EXAMPLE 4
Preparation of Composition Using Red Grape Juice

A sample of Welch's Concorde grape juice (Orpington, UK) was used for the trial. It contained 2.5 g/L polyphenols and had a dry weight of 177 g/L.

A comparison of two resins, Diaion™ HP-20 and Sepabead™ SP70 (Mitsubishi, N.Y.) was made. For the HP20 resin the treatment was similar to that in Example 2 except that the grape juice was not dealcoholised. Grape juice (250 ml) was added to 50 g HP20 or SP70 absorbent. The column was washed with water (4 bv) to remove sugars and the polyphenols eluted with 125 ml 75% aqueous ethanol. The eluent was made up to the original volume of the grape juice (250 ml) with water. For the HP20 absorbent, the polyphenol content of the eluent was 1.65 g/L. The dry weight of the diluted eluent was 2.27 g/L and the solid had a polyphenol content of 72.6%.

Exactly the same procedure was conducted using the SP70 absorbent. In this case the polyphenol content of the eluent was 1.53 g/L, the dry weight of the eluent was 2.09 g/L and the polyphenol content of the dry solid was 73.1%.

Table 3 shows the results of analyzing a sample of the red grape juice, and the eluents from the HP20 and SP70 absorbents. Since the eluents were made up with water to the original volume of the grape juice used, the analyses can be directly compared. The grape juice has a high concentration of flavonols amounting to 41.7 mg aglycone/L most of which were glycosides. As expected the concentration of the aglycone was low, being only 0.7 mg/L, because the aglycone is only found in high concentration in fermented grape juice, for example red wine.

Using 75% aqueous ethanol as the eluting solvent, the yield of flavonol was very high and the concentration of flavonol in the eluent virtually identical to the original grape juice (allowing for experimental error). There was no apparent

TABLE 3

Polyphenol concentrations in
red grape juice and eluent from HP20 and SP70 abosrbents

| Polyphenol* | Red Grape Juice mg/L | Eluent from HP20 mg/L | Eluent from SP70 mg/L |
|---|---|---|---|
| 1 gallic acid | 7.1 | 0.4 | 1.7 |
| 2 procyanin dimers | 10.6 | 13.7 | 11.3 |
| 3 catechin | 15.7 | 12.1 | 16.1 |
| 4 epicatechin | 7.5 | 6.7 | 6.6 |
| 5 polymeric paenols | 277 | 252 | 221 |
| 6 caftaric acid | 49.3 | 25.8 | 36.6 |
| 7 caffeic acid | 3.6 | 3.2 | 3.6 |
| 8 coutaric acid | 12.6 | 9.9 | 12.3 |
| 9 p-coumaric acid | 2.1 | 1.9 | 1.7 |
| 10 trans resveratrol | <0.1 | <0.1 | <0.1 |
| 11 cis resveratrol | <0.1 | <0.1 | <0.1 |
| 12 myricetin glycosides | 28.4 | 27.9 | 29.8 |
| 13 quercetin glycosides | 33.0 | 34.0 | 33.5 |
| 14 myricetin | 0.3 | 0.4 | 0.4 |
| 15 quercetin | 0.3 | 0.3 | 0.2 |
| 16 delphinidia glycoside | 1.0 | 1.6 | 1.2 |
| 17 peonidin glycoside | 2.9 | 3.9 | 4.7 |
| 18 petunidin glycoside | 1.3 | 1.5 | 1.0 |
| 19 malvidin glycoside | 3.1 | 2.7 | 2.2 |
| 20 polymeric anthocyanins | 13.2 | 12.4 | 10.7 |
| 21 delphinidin diglucoside | 1.7 | 1.1 | 1.0 |
| 22 cyanidin diglucoside | 4.3 | 5.6 | 5.9 |
| 23 peonidin diglucoside | 9.8 | 11.7 | 11.3 |
| 24 petunidin diglucoside | 1.7 | 2.5 | 2.4 |
| 25 malvidin diglucoside | 4.5 | 5.0 | 3.7 |

*Peak 1 was quantified as gallic acid, peaks 2, 3, 4, 5, 27 and 27 as catechin, peaks 6 through 9 as caffeic acid, peaks 10 and 11 as trans resveratrol, peaks 12 and 13 as quercetrin, peaks 14 and 15 as quercetin, and peaks 16 through 25 as malvin.
+made up to same volume as original grape juice with water difference between the HP20 and SP70 absorbents in their efficacy to remove flavonols. For the HP20 absorbent the calculated flavonol content of the dry powder as 25.1 mg aglycone/g polyphenol (2.51%) and for the SP70 absorbent it was 28.1 mg aglycone/g polyphenols (2.81%).

To 50 ml eluent from the SP70 absorbent 5 mg rutin (quercitin-3-rutinoside, Sigma, UK) was added and the mixture warmed to 70° with stirring to dissolve. The solution was then evaporated to dryness in vacuo to give 110 mg of red powder containing 70% polyphenols. To another 50 ml was added 2 mg quercitin and the solution treated as before to give a red powder, with similar polyphenol content. Both red powders were readily soluble in water at room temperature but required heating to dissolve completely.

EXAMPLE 5
Preparation from Pomace

About 2000 Kg pomace obtained from white grapes was well stirred in a commercial mixer with 2500 L distilled water at 30° C. for four hours. The mixture was then removed from the mixer and placed in a tank and allowed to settle for two hours, the supernatant was then drawn off and filtered to give a clear liquid. The same procedure was then employed as in Example 3 for absorption of the polyphenols using 65 L of Diaion™ HP-20 resin in a large column, washing with water and eluting with 250 L 50% v/v aqueous ethanol.

On concentration of the aqueous ethanol solution to 35% volume a red colored solid appeared weighing approximately 600 g. This was soluble in 10% aqueous alcohol and was the spray dried to give a solid insoluble in water but soluble in aqueous alcohol. The remaining solution was then spray dried under nitrogen to give 1.4K of a red colored material containing about 50% w/w polyphenols.

This method has the disadvantage that the procedure to obtain the extract before absorption on the resin is more difficult and time consuming. Although the yield was less, the availability of grape skins cheaply has commercial advantages. It was possible to enrich this material with added flavonol.

What is claimed is:

1. A method of producing a dry polyphenol containing composition comprising flavonols and anthocyanins for human consumption comprising:

a) using a grape extract wherein said extract contains sufficient flavonols to yield at least 1% w/dry wt flavonols;

b) applying said grape extract to a solid chromatographic separation medium which retains polyphenols;

c) eluting material from the separation medium with a liquid eluent acceptable for the preparation of foods;

d) recovering a fraction in which the polyphenols are present, wherein said recovered polyphenol fraction comprise at least 25% w/dry wt polyphenols and 1% w/dry wt flavonols and about 1% w/dry wt anthocyanins;

e) drying the recovered polyphenol fraction.

2. A method according to claim 1, in which the liquid grape extract comprises at least one member selected from the group consisting of grape juice, wine, dealcoholised wine, grape skins, and fermented grape skins.

3. A method according to claim 1, wherein the separation medium comprises a polymeric chromatographic column.

4. A method according to claim 1, wherein the separation medium comprises a synthetic polymeric resin.

5. A method according to claim 3, wherein the polymeric resin comprises polystyrene.

6. A method according to claim 1, wherein the drying step comprises spray-drying.

7. A method according to claim 1, wherein the eluent comprises at least one member selected from the group consisting of: water, methanol, ethanol, acetone, ethyl acetate, methylene dichloride and chloroform.

8. A method according to claim 1, resulting in a recovered composition comprising at least 35% w/w of the polyphenols.

9. A method according to claim 1, resulting in a recovered composition comprising at least 45% w/w polyphenols.

10. A method according to claim 1, resulting in a recovered composition in which flavonols comprise at least 4% w/w of the polyphenols.

11. The method of claim 1, wherein said grape extract contains sufficient flavonols to yield at least 2% w/dry wt total polyphenols and said recovered polyphenols comprise at least 2% w/dry wt total polyphenol.

12. A method according to claim 1 in which the flavonols recovered comprises at least one member select from the group consisting of quercitin, myricetin, kaempferol, and conjugates thereof.

13. A method according to claim 1, wherein the additional flavonol is dissolved in a solvent and added to a solution of the recovered polyphenol fraction and the mixture dried.

14. A method according to claim 13, wherein the additional flavonol is added after drying of the recovered polyphenol fraction.

15. A method according to claim 13, in which the flavonol added are between 0.1 to 80% w/w of the polyphenols.

16. A method according to claim 14, in which the flavonols added are between 0.1 to 80% w/w of the polyphenols.

17. A method according to claim 13, in which the flavonols added are between 1 and 25% w/w of the polyphenols.

18. A method according to claim 15, in which the flavonols added are between 1 and 25% w/w of the polyphenols.

19. A method according to claim 13, in which the flavonol added is quercitin, myricetin, kaempferol or glycosides thereof.

20. A method according to claim 14, in which the flavonol added is quercitin, myricetin or glycosides thereof.

* * * * *